(12) United States Patent
Gordon et al.

(10) Patent No.: US 8,709,750 B2
(45) Date of Patent: Apr. 29, 2014

(54) METHOD FOR PROCESSING AN ALGAE MEDIUM CONTAINING ALGAE MICROORGANISMS TO PRODUCE ALGAL OIL AND BY-PRODUCTS

(75) Inventors: Roman Gordon, Studio City, CA (US); Igor Gorodnitsky, Marina del Rey, CA (US); Varvara Grichko, Riverside, CA (US)

(73) Assignee: Cavitation Technologies, Inc., Chatsworth, CA (US)

( * ) Notice: Subject to any disclaimer, the term of this patent is extended or adjusted under 35 U.S.C. 154(b) by 984 days.

(21) Appl. No.: 12/637,065

(22) Filed: Dec. 14, 2009

(65) Prior Publication Data

US 2010/0151540 A1 Jun. 17, 2010

Related U.S. Application Data

(63) Continuation-in-part of application No. 12/395,110, filed on Feb. 27, 2009, now Pat. No. 7,762,715, and a continuation-in-part of application No. 12/464,646, filed on May 12, 2009, now Pat. No. 8,042,989.

(60) Provisional application No. 61/122,636, filed on Dec. 15, 2008.

(51) Int. Cl.
*C12P 1/00* (2006.01)

(52) U.S. Cl.
USPC ........ 435/41; 435/243; 435/257.1; 435/293.2

(58) Field of Classification Search
None
See application file for complete search history.

(56) References Cited

U.S. PATENT DOCUMENTS

| | | | | |
|---|---|---|---|---|
| 3,902,273 A | * | 9/1975 | Friedman | 47/58.1 R |
| 5,164,308 A | | 11/1992 | Kyle | |
| 5,198,122 A | * | 3/1993 | Koszalka et al. | 210/748.04 |
| 5,318,570 A | * | 6/1994 | Hood et al. | 606/99 |
| 6,000,551 A | * | 12/1999 | Kanel et al. | 209/164 |
| 6,221,260 B1 | * | 4/2001 | Chahine et al. | 210/748.11 |
| 6,279,611 B2 | * | 8/2001 | Uematsu et al. | 137/888 |
| 7,135,308 B1 | * | 11/2006 | Bush et al. | 435/42 |
| 7,207,712 B2 | | 4/2007 | Kozyuk | |
| 2006/0024404 A1 | * | 2/2006 | Kyle | 426/2 |
| 2006/0050608 A1 | * | 3/2006 | Kozyuk | 366/176.2 |
| 2007/0014186 A1 | * | 1/2007 | Mattison et al. | 366/149 |
| 2007/0048848 A1 | | 3/2007 | Sears | |
| 2007/0189114 A1 | | 8/2007 | Reiner et al. | |
| 2008/0220515 A1 | | 9/2008 | McCall | |
| 2009/0152212 A1 | * | 6/2009 | Kelsey et al. | 210/787 |

OTHER PUBLICATIONS

Niemczewski, Ultrasonics Sonochemistry 6:211-216 (1999).*
Bajpai et al ., J. Oleo Sci., vol. 55, No. 10, 487-502 (2006).*
Grima et al., Biotechnol. Advan., 20:491-515 (2003).*
Christi, Biotechnol. Advan., 25:294-306 (2007).*
Huber et al., Chem. Rev. 106:4044-4098 (2006).*

(Continued)

Primary Examiner — Blaine Lankford
Assistant Examiner — Thomas J Visone
(74) Attorney, Agent, or Firm — Kelly & Kelley, LLP (57) ABSTRACT

A device and method for processing an algae medium containing algae microorganisms to produce algal oil and by-products thereof. The method comprises pumping the algae medium through a flow-through hydrodynamic cavitation device, generating localized zones of reduced fluid pressure, creating cavitational features in the algae medium, collapsing those cavitation features, and disintegrating cell walls and intracellular organelles to produce algal oil and by-products.

19 Claims, 8 Drawing Sheets

(56) References Cited

OTHER PUBLICATIONS

Liu et al., J. Chem. Technol. Biotechnol., 82: 775-780, Abstract Only (2007).*
Save et al., Food Bioprod. Process., 75(1):41-49 (1997).*
Blaser et al., Luminescence;17:370-380 (2002).*
Sawant et al., Biochem. Eng. J. 42:320-328 (2008).*

* cited by examiner

(a) before          (b) after

FIG. 18

METHOD FOR PROCESSING AN ALGAE MEDIUM CONTAINING ALGAE MICROORGANISMS TO PRODUCE ALGAL OIL AND BY-PRODUCTS

BACKGROUND OF THE INVENTION

The invention relates generally to cavitation-assisted methods that are used for processing heterogeneous media and mixtures via formation of cavitation bubbles that represent distinct mini-reactors, and uses the energy released upon implosion of these cavities to modify said fluids. The device and method may find applications in biofuel production, chemical, pharmaceutical, food and other industries.

More particularly, the invention relates to the disintegration of unicellular and/or multicellular algal microorganisms and their intracellular organelles to release oil and other cell contents and recover the ingredients. The invention utilizes the implosion energy of cavities to break either reversibly or irreversibly the cell walls and/or membranes of the microorganisms and organelles to release their biochemical constituents, followed by their separation and subsequent conversion into modified, more valuable products, i.e., algal oil.

Biodiesel is an alternative fuel, as it has been designated by the U.S. Department of Energy and the Department of Transportation, and is registered with the U.S. EPA as a fuel. It is biodegradable ester-based fuel that is used as a substitute for petroleum diesel. In the B20 blend (20% biodiesel and 80% petroleum diesel), biodiesel significantly reduces emissions and the level of toxic contaminants in exhaust. Biodiesel can be used in any diesel engine, without the need for mechanical alterations. In practice, biodiesel is manufactured from vegetable oils, animal fats, greases, or other sources of triglycerides by a catalyst-assisted transesterification of triglycerides with methanol, ethanol or by similar methods. The usage of the flow-through hydrodynamic devices greatly increases the reaction rate, improving the yield and composition of the produced biodiesel.

Algal oil is a valuable agricultural land-saving alternative to plant feedstock, such as soybean oil, canola and palm oil or animal, fish and bird fat and tallow. Algae are the simplest plants that live in a water environment. Many algae are unicellular that may or may not have a cell wall. Similar to other plants, algae are photosynthetic. They utilize carbon dioxide as a carbon source and store energy in the form of lipids within the intracellular oil bodies, surrounded by membranes (Barsanti and Gualtieri, 2006). Algae multiply and grow at a very fast rate and, depending on the genetic background and growth conditions, may have very high oil content. In biodiesel production, the wild type strains of algae or mutants and genetically modified microorganisms, which are designed and selected to produce enhanced levels of oil and/or high levels of oleic acid, are preferred. Such strains can be obtained by PCR mutagenesis or by exposure to ultraviolet or ionizing radiation and chemical mutagens. Oil-overproducing strains can be engineered with the help of the directed evolution and other biotechnological techniques known to those skilled in the art (Glick and Pasternak, 2003). More methods to transform algae are disclosed in U.S. Pat. No. 5,661,017 to Dunahay et al.

The process involves the cultivation of microorganisms capable of producing the algal oils in an appropriately controlled environment, wherein the cells are properly treated to stimulate production of oil. Algae produce substantial amount of triacylglycerols as a storage lipid under photo-oxidative stress, nitrogen depletion or other adverse environmental conditions. The produced oil is preferably enriched in oleic acid. Synthesis and sequestration of oil into cytosolic lipid bodies appear to be a protective mechanism by which algal microorganisms cope with stress conditions. Fatty acids, the building blocks for triglycerides, are synthesized in the chloroplast. Acetyl CoA carboxylase is a key enzyme in regulating the rate of fatty acid synthesis. (Hu et al., 2008)

The U.S. DOE Aquatic Species Program has studied algae for twenty years and reported that the algae species can produce up to 60% of their body weight in the form of triglycerides. The complete report is available at http://www.ott.doe.gov/biofuels/pds/biodiesel from algae ps.pdf. In some species of algae, the oil may account for more than half of the cellular mass, which corresponds to more than 80% of the cell dry weight (Molina et al., 2003) [Molina Grima E, Belarbi E-H, Acién Fernández F G, Robles Medina A, Chisti Y (2003) Recovery of microalgal biomass and metabolites: Process options and economics. Biotechnol. Adv. 20: 491-515]. In comparison to agricultural crops, algae-based technology yields significantly more oil per acre. For example, soybean and rapeseed generate about 50 and 130 gallons of oil per acre, respectively, while algae yields up to 10,000 gallons of oil per acre of the water reservoir. Thus, algae, namely diatoms and green algae, are considered to be a promising sustainable feedstock for the production of oil and biodiesel.

There are a number of methods for disintegration of algae and recovering the algal oil, such as bead-assisted milling, pressing, extraction with organic solvents, enzymatic degradation, lysis using osmosis and ultrasonic and microwave-assisted disruption (Cravotto et al., 2008). In most practical applications, the dried and broken cells are extracted with a suitable solvent, preferably hexane, for about two days. The average consumption of hexane is about 5 liters per kilogram of biomass (U.S. Pat. No. 5,164,308 to Kyle). Typically, the crude green oil contains contaminants, such as diglycerides, chlorophyll and other pigments and sterol esters and should be purified until the light yellow oil composed mainly of triglycerides is obtained.

If desired, the cells can be broken, using ultrasonic techniques. Sonication generates cavitation bubbles that collapse violently during a high-pressure cycle. During the implosion of these cavities, very high pressure and temperature and high-speed jets are produced. The resulting shear forces break the cell walls and intracellular organelle membranes, releasing triglycerides into the surrounding fluid, usually hexane or cyclohexane. After the oil is fully dissolved in the organic solvent, the cell debris is filtered out and the solvent is distilled off to recover the oil. However, the cavitation induced by sound waves in the acoustic range (20 Hz-20 KHz) or the ultrasound range (>20 KHz) does not offer an optimized method for cell disruption. For instance, the intensity threshold of ultrasound cavitation in water is >0.3 W/cm$^2$. The typical power requirements for the ultrasonic device integrated inline is approximately 1000 kW for 20-100 m$^3$/h flows.

U.S. Pat. No. 5,629,185 to Stanzl et al. discloses a process for disintegrating dispersions or suspensions of algal microorganisms using ultrasonication for the purpose of recovering cellular constituents. The selected parameters that include sonotrode immersion angle and length of immersion, ratio of sonotrode immersion relative to the acoustic irradiation volume and the ratio of extent of immersion to the solid content of the medium to be sonicated permit the establishment of a particular geometry form for the acoustic irradiation container and method optimization.

The main disadvantage of the sonication technology is the batch environment. Since the effect of sonication diminishes with an increase in distance from the radiation source, the treatment efficacy depends on the size of the irradiation container and is low with large vessels. Sonication disruption cannot be used efficiently in many continuous processes because the energy density and the required residence time would be insufficient for the high throughput of a continuous process. A residence time of about one hour is typically needed for batch process completion. In addition, the alterations are not uniform and occur at particular locations, depending on the frequency of the radiation and the interference pattern. Thus, the efficacy of the sound disruption is further lowered.

High-shear technologies of cell disruption that are used in large-scale production employ the rotor-stator, valve-type or fixed-geometry processors. In these devices, cell broths are subjected to shear forces that pull cells apart. The rotor-stator method is not suitable for the difficult-to-lyse cells and provides highly variable yields. The valve-type disruptors (French press or pumped-fluid processor) destroy cells by forcing the cell-enriched medium through a valve at a pressure of 20-30 Kpsi or higher. The shear force is regulated by controlling the pressure and valve tension. With cultures requiring multiple treatments, cooling is generally required. In the French press, a hydraulic pump drives a piston within a cylindrical body filled with the sample to squeeze it past a needle valve. Once past the valve, the pressure drops, generating shear forces that destroys cells. The device is not suited for processing large volumes and is hard to clean. The mechanically pumped-fluid processors force the medium at a constant volume flow past a spring-loaded valve and are prone to valve clogging. The fixed-geometry processors disrupt microorganisms and cells by forcing them at a high pressure through a chamber that houses a narrow channel and allows controlled cell breakage without using detergents or salts. The fixed geometry of the chamber provides superior reproducibility, while requiring fewer passes.

It has been found that flow-through hydrodynamic cavitation can disintegrate algal cells, allowing fast and efficient release of all intracellular oil. It is well known that a drastic increase in both pressure and temperature and vigorous mixing provided by either acoustic or hydrodynamic cavitation initiates and accelerates numerous reactions and processes. Enhancing the reaction yields and process outcomes by means of the energy released upon the collapse of cavities in a liquid medium has found numerous applications in synthesis, expedition of chemical reactions, homogenizing and other technologies. Although extreme pressure or tremendous heat can be detrimental, the outcome of the optimized cavitation treatment is often beneficial.

Cavitation can be of many different origins, for example, hydrodynamic, acoustic, laser-induced or can be generated by injecting steam into a sub-cooled fluid, which produces collapse conditions similar to those of hydrodynamic and acoustic cavitations (Young, 1999; Gogate, 2008; Mahulkar et al., 2008). Coupling of two or more cavitation-generating techniques provides even better results. For example, direct steam injection coupled with acoustic cavitation increases treatment efficiency by sixteen times, as compared to acoustic cavitation alone.

When fluid temperature approaches the boiling point, the formation of bubbles becomes noticeable. If fluid is pumped through a hydrodynamic cavitation apparatus with a pump at the proper flow velocity, as a result of the decreased hydrostatic pressure (Bernoulli's principle), vapor filled cavitation bubbles form at a concentration of hundreds in one milliliter. The bubbles take up space normally occupied by fluid resisting the flow and increasing the pressure. The formation and growth of the cavities can be prevented by an increase in pressure. When the vapor-filled cavities relocate to a slow-velocity/high-pressure zone, they collapse within $10^{-8}$-$10^{-6}$ s. The implosion results in a localized sharp increase in both pressure and temperature, i.e., as much as 1,000 atm and 5,000° C. or more, and produces local jet streams with velocities reaching 100 m/s and higher (Suslick, 1989; Didenko et al., 1999; Suslick et al., 1999; Young, 1999). The collapse of the cavities generates shock waves, vigorous shearing forces and heat, and releases a substantial amount of energy, which activates atoms, molecules and radicals located within the bubbles and in the surrounding fluid, and initiates chemical reactions and processes and/or dissipates into the surrounding. In many cases, the implosion is light emission-free. In other cases, it is coincidental with the emission of ultraviolet and/or visible light, which may favour photochemical reactions or generate radicals (Zhang et al., 2008). A side effect of the excessively high pressure is heat release, which may become a problem if overheating is detrimental to product's quality and cavitation device operation safety.

The cavitation phenomenon is categorized by the dimensionless cavitation number $C_v$, defined as: $C=(P-P_v)/0.5\rho V^2$, where P is the recovered pressure downstream of a constriction, $P_v$ is the vapor pressure of the fluid, V is an average velocity of fluid at the constriction, and $\rho$ is the fluid density. The cavitation number, at which the cavitation starts, is defined as the cavitation inception number $C_{vi}$. Cavitation ideally begins at $C_{vi}=1$. Another important term is the processing ratio, which is a number of cavitation events in a unit of flow. The smaller the bubble, the greater the energy released during its implosion. The effect of surface tension and size of cavities on the hydrostatic pressure is defined as follows: $P_i=P_0+2a/R$, where $P_i$ is the hydrostatic pressure, a is the surface tension, and R is the radius of the bubble (Gogate, 2008; Passandideh-Fard and Roohi, 2008).

The flow-through hydrodynamic cavitation does not require using a batch container, as does sound or ultrasound-induced cavitation. Numerous flow-through hydrodynamic devices are known. See, for example, U.S. Pat. No. 6,705,396 to Ivannikov et al., U.S. Pat. Nos. 7,338,551, 7,207,712, 6502, 979, 5,971,601 and 5,969,207 to Kozyuk, which disclose different hydrodynamic cavitation reactors and their applications.

Liquid cell cultures are viscous media, and flow-through hydrodynamic cavitation is very profound in such fluids. If a high-cell-density broth is fed into the cavitation device at a proper velocity, causing a flow pressure to drop below the solvent's vapor pressure, cavitation will occur. The cavitation temporarily separates the high-boiling-point compounds and particles from the entrapped gases, water vapor and the vapors of the affected fluids that can be found in the bubbles. Small particulate and impurities serve as nuclei of the cavitation bubbles that may reach a few millimeters in diameter, depending on the conditions. The implosion of the cavities breaks cells, releases their contents into the surrounding fluid and mixes them with the solvent. The temperature, composition and pH of the medium to be treated can be adjusted to increase the efficiency of the oil recovery. In general, the optimization will depend on the cell structure of the species, the composition of the extracting medium, and the presence of contaminants.

To lower the release of unwanted intracellular constituents, including the cell wall debris or products of the denaturation, it is desirable to control cell breakage. The flow-through hydrodynamic cavitation process has a low residence time and does not require much solvent, reducing the chance of denaturation and decomposition of targeted compounds and valuable by-products, lowering downstream production cost and improving the environmental effect.

Algal cell walls contain glycoproteins, sporopollenin, calcium, cellulose and other polysaccharides that are used for algal taxonomy. The diatoms synthesize their cell walls from orthosilicic acid. The cell membrane that lies under the cell wall is a selectively permeable lipid bilayer, which is found in all cells. Algal microorganisms often exhibit high stability and resistance to degradation by enzymes and strong chemical reagents. Therefore, the disintegration of algae with the controlled flow-through hydrodynamic cavitation process may be combined with the enzymatic, chemical or other lysis to achieve a synergetic effect. Hydrodynamic cavitation assists protease, lipase, cellulase, amylase, lysozyme, lysostaphin, zymolase, mutanolysin, glycanase, mannase and other enzymes in penetrating and degrading the cell walls and membranes, resulting in an improved extraction of oil with higher yields. The process can be scaled up easily to accommodate large process streams.

At the present time, with the cost of energy rising rapidly, it is highly desirable to shorten processing time and lower energy consumption to secure as large a profit margin as possible. However, the prior art techniques do not offer the most efficient method of algal cell disruption, especially the hard-to-break species, in the shortest amount of time possible. A need, therefore, exists for the advanced flow-through device for processing algae broth with a minimal residence time and energy cost resulting in oil-containing mixtures with improved characteristics that can be easier to purify. The advanced, compact, and efficient apparatus is particularly desired at the algae growth locations and in field conditions, when throughput is a key factor. The present invention provides such a device, while delivering intracellular oil and other valuable constituents and by-products within a short time.

SUMMARY OF THE INVENTION

The present invention provides a method and device for disruption of various algal microorganisms (both unicellular and multicellular) by generating cavitation in a liquid culture flow within at least one cavitation chamber. This goal is achieved through the design of a flow-through hydrodynamic cavitation device aimed at fast cell breakage and recovery of the intracellular contents.

In accordance with the present invention, the method comprises feeding an algae-enriched liquid broth into a flow-through hydrodynamic cavitation device, applying a desired inlet pressure sustained by a pump and using digestive reagents and conditions of choice.

The present invention is directed to a method for processing an algae medium containing algae microorganisms to produce algal oil and by-products. The method begins with pumping the algae medium through a flowpath in a multi-stage, flow-through, hydrodynamics cavitation device. Localized zones of reduced fluid pressure are generated in the algae medium as it is pumped through the flowpath. Cavitation features are then created in the algae medium in the localized zones of reduced fluid pressure. Those cavitation features are then collapsed to expose components of the algae medium in the cavitational features and the surrounding fluid to sudden, localized increases in temperature and pressure. These localized increases in temperature and pressure result in the disintegration of cell walls of and intracellular organelles in the algae microorganisms in the algae medium to produce algal oil and by-products. The algal oil is then separated from the algal medium for further processing. The generating, creating, collapsing and disintegrating steps may be repeated as necessary to achieve a desired degree of disintegration.

The algae medium preferably comprises a heterogeneous, complex mixture containing species of algae microorganisms, including wild-type, mutated or genetically altered, or a mixture thereof. The algae microorganisms may be vital, vegetative, dead, dried, intact and/or broken. The algae medium may also be a multi-phase system comprising unmixable liquids, a solution of salts, gasses and/or solutes, a dispersion, an emulsion, a suspension, a melted solid, a gas in a supercritical state, or a mixture thereof. The algae medium preferably comprises algal microorganisms suspended in methanol, ethanol, butanol or a mixture thereof.

The method may also include the step of adding vegetable oil and/or animal fat or tallow. In addition, other materials may be added to the algae medium such as hydrogen peroxide, chemical salts, acids, bases, buffers, detergents and/or enzymes to facilitate the disintegration of cell walls and intracellular organelles. A transesterification catalyst may be added so that triglycerides extracted from the algal oil and by-products may be reacted with an alcohol to produce biodiesel.

The inner walls of the flowpath may be roughened to increase disintegration of the cell walls and intracellular organelles. The inner walls of the flowpath are preferably made from or coated with a metal, a metal alloy, a solid transesterification catalyst, or a magnetic material. In the case of a magnetic material, the algae medium may be subjected to an external direct, alternating or pulsed electric and/or magnetic field. Further, a mechanical shock, a heat shock, or other stress may be imposed on the algae microorganisms, to force the algae microorganisms to increase production and accumulation of algal oil. Sonic and/or ultrasonic cavitation may also be applied to the algal medium prior to and/or after the pumping step.

The algae medium may be pre-heated and then pumped at ambient temperature. Bleaching earth may be added to the algae medium to remove contaminants from the algal oil. In addition, air, hydrogen, nitrogen, carbon dioxide or a mixture of gasses may be added—or the algae medium prior may be degassed prior to the pumping step. Microbial yeast, plant and/or animal cells or tissues may also be added to the algae medium.

Accordingly, besides the objects and advantages of the expeditious cell disruption described in this patent application, several objects and advantages of the present invention are:

- to ease operation, improve productivity and reduce energy consumption of culture processing and subsequent cell disruption;
- to provide a continuous flow device for generating cell extracts in a dramatically expedited manner with optimized yields and energy costs;
- to provide a method for mixing and altering algal cell extracts by subjecting them to at least one hydrodynamic cavitation process at an increased temperature, decreasing the cavitation threshold;
- to provide a method for the one-step biodiesel production by subjecting a dried, water-free algal cell suspension in methanol, ethanol, butanol or other suitable solvent or mixture thereof to hydrodynamic cavitation in the presence of a catalyst of choice, followed by subjecting the residual original compounds and the products of trans-esterification to separation and purification or a second cavitation event, if needed;

to provide a device for manipulating algal cells at the site of production;

to provide a rapid method for stressing algae to stimulate oil production resembling the effect of nutrient deficiency or other stimuli;

to produce a uniform cavitation field throughout the fluid medium for a time sufficient to achieve extraction of oil and/or other valuable intracellular ingredients and producing changes in them, if needed; and to provide a method, wherein two or more flow-through hydrodynamic multi- or single-stage cavitation devices can be employed.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The detailed embodiments of the present invention are disclosed herein. However, it should be understood, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and how to use the invention.

With reference to the attached drawings, a method and device for the application of pressure, heat and vigorous mixing to produce algal oil from microorganisms is disclosed. The method and device include using flow-through hydrodynamic cavitation to disintegrate cells, promote extraction of oil and other valuable cellular ingredients and chemical reactions, if needed. These processes and reactions occur in a short time and results in a high yield of oil.

The objects of the present invention are achieved by forcing a fluid medium through a flow-through hydrodynamic cavitation device to disrupt cells, extract oil and induce chemical reactions, if needed. Hydrodynamic cavitation involves the formation of vapor bubbles within a fluid medium accelerated to a proper velocity with a high-pressure pump. The phenomenon is called cavitation, because when the flow pressure reduces to the vapor pressure cavities form in the fluid. The cavities expand as they move into a low-pressure region and collapse in a downstream high-pressure region. The collapse produces a sharp jump in local pressure and temperature along with intense shearing forces, resulting in cellular disruption, mass transfer and chemical reactions. The configuration utilized in a flow-through hydrodynamic cavitation device is an equipment cost decision. A number of approaches are technically feasible for both large and small volume media. To ensure the best yield, the cavitation process should be uniform throughout the fluid flow and the use of excess energy should be minimized. Ideal cavitation should occur efficiently at the minimal energy expenditure.

The present invention uses energy released during the implosion of the cavitation bubbles to disrupt algal microorganisms and extract oil. Hydrodynamic cavitation is the formation of vapor-filled cavities in a fluid flow, which is followed by bubble collapse in a high-pressure zone. In general, the cavitation process comprises the following steps. The fluid flow is pumped into the reactor's inlet passage. In a localized tapered zone, the flow velocity increases, causing its pressure to drop (Bernoulli's principle). This leads to the formation of bubbles filled with the vapors of volatile compounds that boil under the given conditions. When the bubbles move beyond the boundary of the tapered zone, the pressure in the flow increases and the bubbles collapse, exposing the vapors found within them and the layer of the surrounding medium to suddenly high pressures and temperatures, shearing forces, shock waves, acoustic vibration and electromagnetic irradiation. Each bubble serves as an independent mini-reactor, in which cell disruption and cellular content extraction occur. The increased pressure and temperature are significantly higher than those in many other industrial processes. The deeper alteration of the medium results in chemical reactions taking place within the collapsing bubbles and/or in the adjacent layers of fluid. According to the present invention, the method controls the intensity of the cavitation field by using a properly designed device, a suitable inlet pressure and by optimizing properties of the algae-containing medium (chemical composition, temperature, concentration, viscosity, etc). An initially high viscosity of algae cell-enriched media can be lowered by adding solvents, surfactants or a mixture thereof. Cell disintegration and fragmentation of large molecules will further reduce the viscosity.

The beneficial effects gained through the present invention cannot be achieved through sound- or ultrasound-induced cavitation, rotor-stator cell disruption or through other methods in existence because the conditions created in this process simply do not exist and cannot be duplicated by other means. In a sound-induced cavitation, bubbles form a barrier to transmission and attenuate the sound waves due to their scattering and diversion, limiting the effective distance. Furthermore, ultrasonic irradiation modifies cells and/or molecules at specific locations within the medium, depending on the frequency, interference pattern and source power. The present invention overcomes these limitations, disrupting intact cells in a uniform manner. This invention efficiently disrupts cells and extracts their content into the fluid medium by supplying energy through hydrodynamic cavitation sufficient to drive the processes and reactions. Thus, this invention provides a better means of the controlled cell breakage and producing oil extracts of superior quality and homogeny.

The method and system include use of a flow-through hydrodynamic cavitational reactor 30 to facilitate the sudden disintegration of unicellular and/or multicellular algal microorganisms and their intracellular organelles to release oil and other cell contents and extract the ingredients, which occurs in a short period of time and results in an improved yield and purer components to produce biodiesel.

The algae-containing medium, which is processed in the device 30, is preferably comprised of dried algal cells suspended in methanol, ethanol, butanol or a mixture thereof. In addition, detergents or enzymes may be added to facilitate the disintegration of algal microorganisms. After the algal medium has been cavitated, a basic, acidic or any other proper catalyst may be introduced to cause the extracted triglycerides to react with alcohol, thus carrying out the transesterification to produce bio-diesel. The cavitation process may be performed in such a way as to impose a mechanical, heat shock or other stress on the algal microorganisms. Such a process leaves the algal microorganisms vital and forces the effected cells to increase oil production and its accumulation.

The algal microorganisms may also be subjected to freezing temperatures prior to being processed in the cavitation reactor 30. Bleaching earth may also be added to the algal medium to remove contaminants from the crude algal oil. The beneficial effects of cavitation processing may be enhanced through the addition of air, hydrogen, nitrogen, carbon dioxide, other similar gases or mixtures thereof. Alternatively, the algal medium may be degassed before being subjected to cavitation. Microbial, yeast, plant or animal cells or tissues may be introduced to algal medium prior to cavitation. Further, vegetable oil, animal fat, fish or bird fat, or tallow may be introduced to increase the yield of the transesterification process. The cavitation process may be performed in the presence of hydrogen peroxide to facilitate cell breakage and carryout the oxidation and other reactions.

When algal microorganisms are disrupted by cavitation, the cavitation bubbles are composed of the solvent vapor. It may be water, hexane, methanol or another solvent or mixture thereof, depending on the application goal. The implosion of these cavities generates energy that breaks cellular walls and/or membranes, releasing oil and other cellular components, if any, into the surrounding and heats the medium. The processed medium contains algal oil, extracted from the broken cells, the cell debris and other components.

Figure 1:
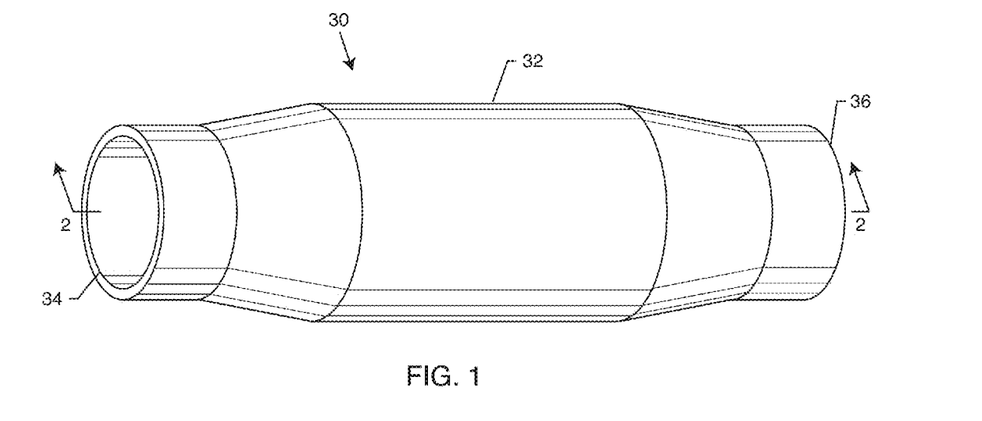
FIG. 1 is a diagram depicting a preferred embodiment of the inventive multi-stage cavitation device.
Figure 2:
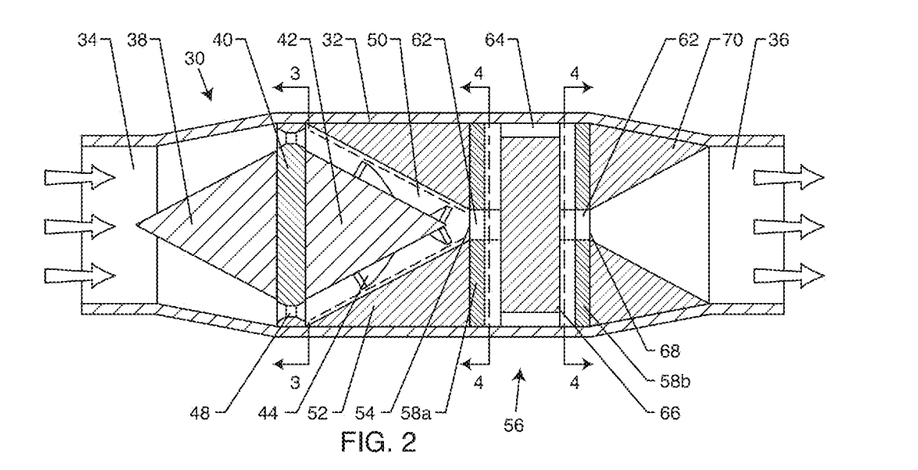
FIG. 2 is a cross-sectional view of the multi-stage cavitation device taken along line 2-2 of FIG. 1.
Figure 3:
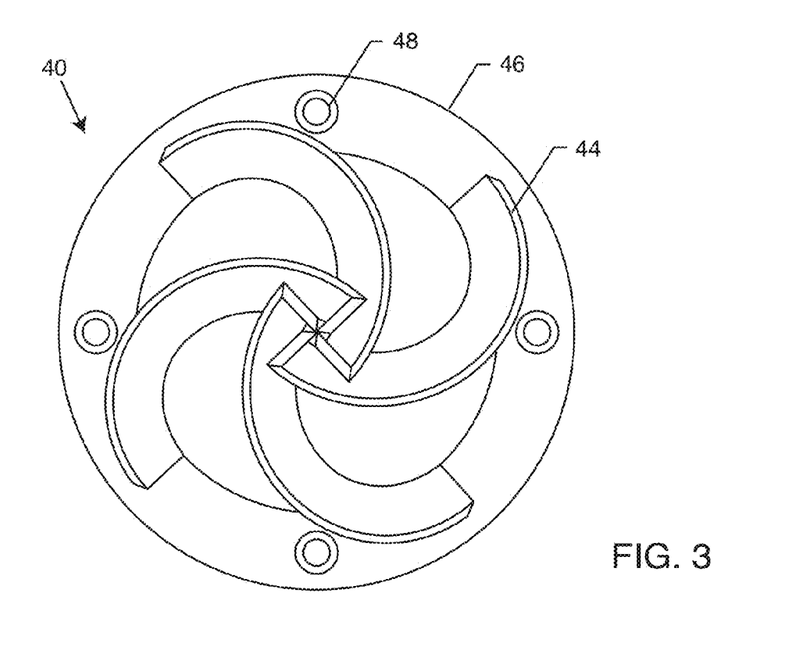
FIG. 3 is a cross-sectional view of the front end of the working chamber of the cavitation system taken along line 3-3 in FIG. 2.
Figure 4:
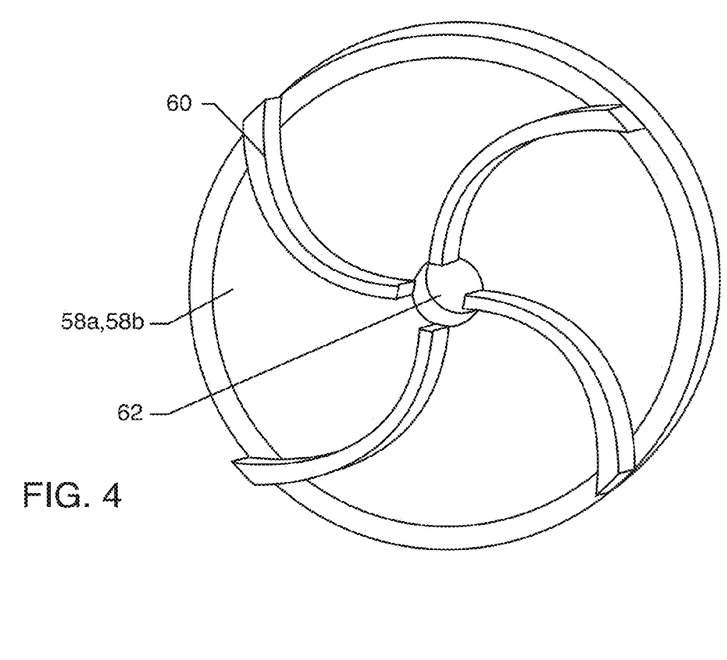
FIG. 4 is a cross-sectional view of the vortex element taken along lines 4-4 in FIG. 2.
Figure 5:
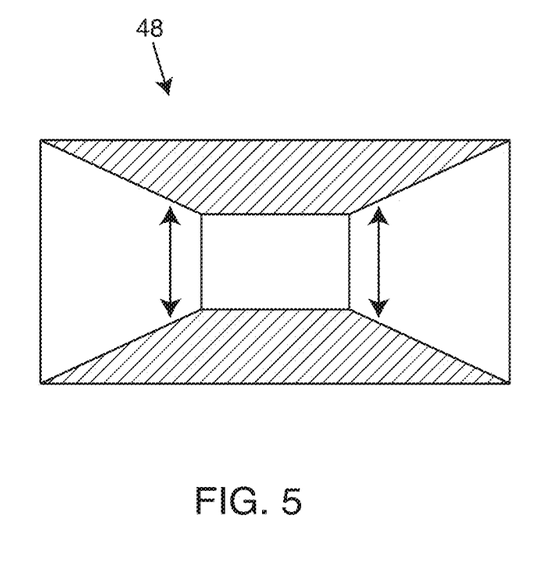
FIG. 5 is a cross-sectional view of one embodiment of a channel in a multi-jet nozzle.
Figure 6:
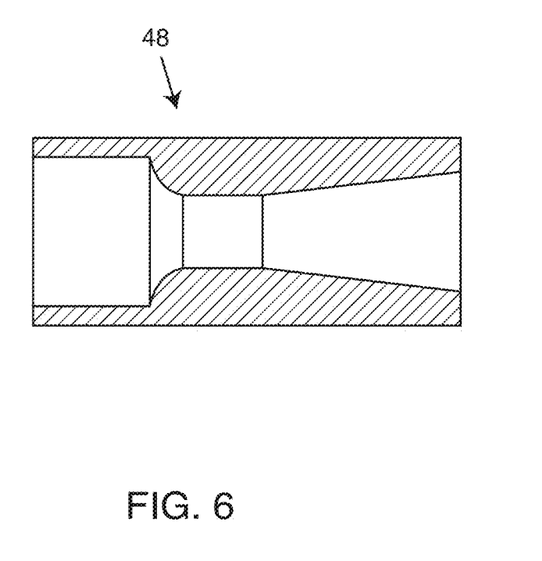
FIG. 6 is a cross-sectional view of an alternative embodiment of a channel in a multi-jet nozzle.

FIGS. 1-6 generally illustrate a first preferred embodiment of the cavitation device 30 of the present invention. This embodiment is described in co-pending U.S. patent application Ser. No. 12/359,110, the disclosure of which is incorporated herein, in its entirety. As shown in FIG. 1, the cavitation device 30 is comprised of a cylindrical body 32 made preferably of a metal, an inlet tube 34 and an outlet tube 36. An inlet cone 38 is located in front of a multi-jet nozzle 40 along the flow path. A guide cone 42 is positioned behind the nozzle 40 and features spiral guides 44. The multi-jet nozzle 40 is shaped as a disk having a perimeter ring 46 and features four channels 48 that have both across abrupt contractions and expansions (FIGS. 2 and 3). The number of spiral guides 44 is equal to the number of channels 48 in the multi-jet nozzle 40. The channels 48 have varying diameters along their lengths (FIGS. 5 and 6) and are uniformly distributed throughout the surface area of the perimeter ring 46 of the multi-jet nozzle 40 and direct flow into the working chamber 50.

The working chamber 50 is located behind the multi-jet nozzle 40 along the flow path and has an inner wall formed by the guide cone 42 and an outer wall formed by a convergent cone 52. The convergent cone 52 is co-axially aligned with the guide cone 42. An outlet 54 from the convergent cone 52 leads to a vortex chamber or generator 56, which is disposed behind the convergent cone 52. The vortex generator 56 is comprised of disks 58 with curved flow guides 60 and central holes 62 that are coaxially aligned with one another. An annular gap 64 is located between the front and rear disks 58*a*, 58*b* and around a cylinder-type body 66 of slightly smaller diameter than the vortex chamber 56 that blocks the direct path of the jet emerging from the central hole 62 in the front disk 58*a*. The curved flow guides 60 are raised with respect to the disks 58 so as to extend out to the cylinder type body 66.

The flow guides 60 create multiple curved flow paths from the central hole 62 in the front disk 58*a* to the annular gap 64 of the vortex generator 56. Similar paths are created from the annular gap 64 of the vortex chamber 56 to the central hole 36 on the rear disk 58*b* on the backside of the cylinder-type body 66. The central holes 36, the outlet 54 of the convergent cone 52 and an inlet 68 of the atomizing cone 70, which is situated behind the vortex generator 56 along the flow path, all have the same diameters.

In this embodiment, the first stage cavitation carried out in the working chamber 50 is at the inlet pump pressure, which encourages formation of cavities composed of solvent(s) only. The second stage cavitation carried out in the vortex chamber 56 involves the formation of cavitation bubbles composed mainly of solvent(s) and/or cell constituent(s). The third stage cavitation is carried out in the atomizing cone 70 and involves the formation of cavitation bubbles composed of high-boiling-point compounds and/or products of the prior cavitation processes.

Figure 7:
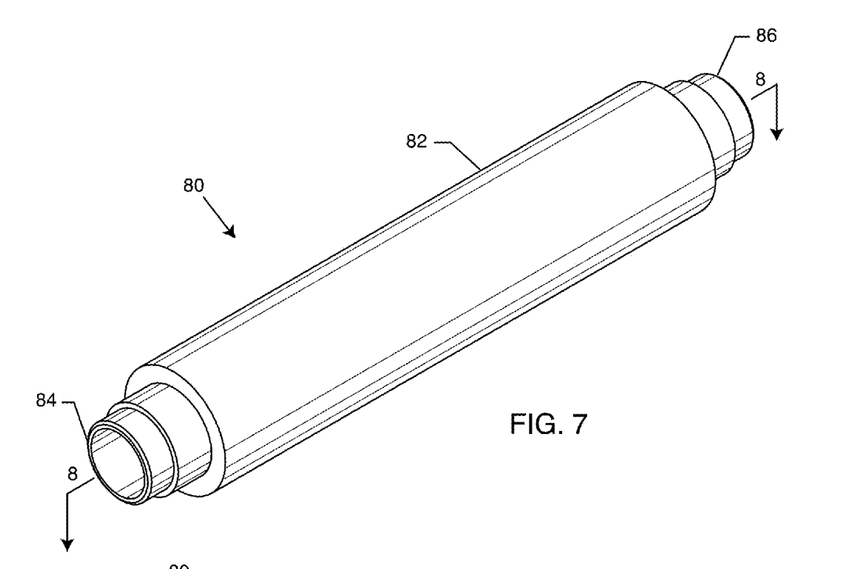
FIG. 7 is a perspective view another preferred embodiment of the inventive multi-stage cavitation device.

FIGS. 7-17 generally illustrate a second preferred embodiment of the cavitation device 80 of the present invention. This embodiment is described in co-pending U.S. patent application Ser. No. 12/464,646, the disclosure of which is incorporated herein, in its entirety. As shown in FIG. 7, the flow-through cavitation device 80 is comprised of a housing 82, which is attached to inlet 84 and outlet 86 pipes for direct connection to an industrial pipeline (not shown). The device 80 preferably has a mirrored symmetry such that from the inlet 84 to a mid-point 88 is repeated in reverse from the mid-point 88 to the outlet 86. The following description will follow the mirrored symmetry and describe from both the inlet 84 and outlet 86 toward the mid-point 88 simultaneously.

Figure 8:
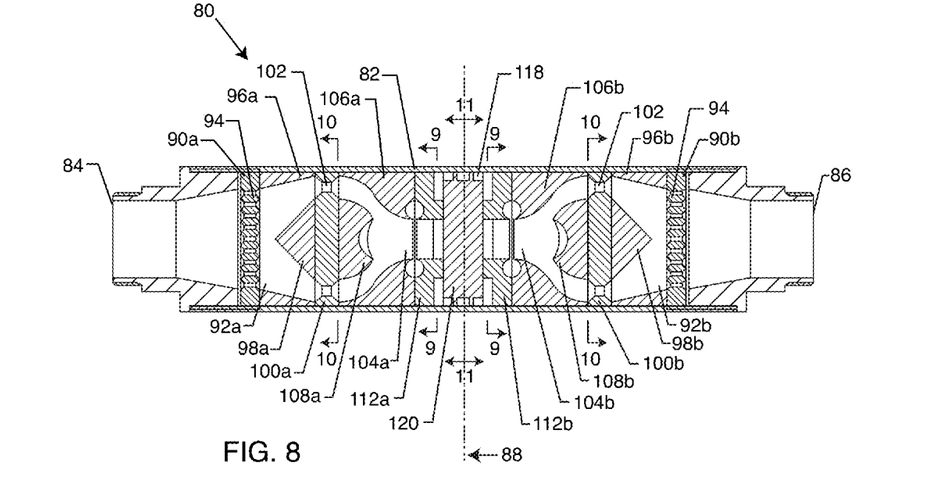
FIG. 8 is a cross-sectional view taken along line 8-8 of FIG. 7.

Assuming flow from left to right, front and end disk multi-jet nozzles 90*a*, 90*b* serve as the front and back walls of exterior working chambers 92*a*, 92*b* and are located behind the inlet pipe 84 and in front of the outlet pipe 86. The multi-jet nozzles 92 are equipped with constricting and expanding channels 94 that are distributed uniformly over the surfaces of the disks that are the multi-jet nozzles 90. The working chambers 92 are comprised of radial cones 96*a*, 96*b* and central guide cones 98*a*, 98*b*, which are attached to radial multi-jet nozzles 100a, 100b. The radial multi-jet nozzles 100 feature both constricting and expanding channels 102. The channels 102 are spread evenly over the radial perimeter surface of the radial nozzles 100, which direct the flow to interior working chambers 104a, 104b.

Flow guides 106a, 106b that direct the flowpath from the perimeter to a center of the device 80 bound the chambers 104. The cross-section of the flow guides 106 generally has an S-shape configuration. A hemi-spherical body 108a, 108b with a top niche 110 is mounted in the working chambers 104 against the radial nozzles 100. The turbulizer disk 112a, 112b (FIG. 9) with curved guides 114 and central hole 116 is located behind the guides 106 in vortex chamber 118. The vortex chamber 118 is formed of the inner wall of the housing 82 and a cylindrical body 120 disposed in the center. The vortex chamber 118 directs the flow from the hole 116 of the front disk 112a. The holes 116 in the front and rear disks 112a, 112b are coaxial. Their diameters are equal to that of holes in the guides 106. The mid-point 88 is within the vortex chamber 118.

Figures 9, 10, 11:
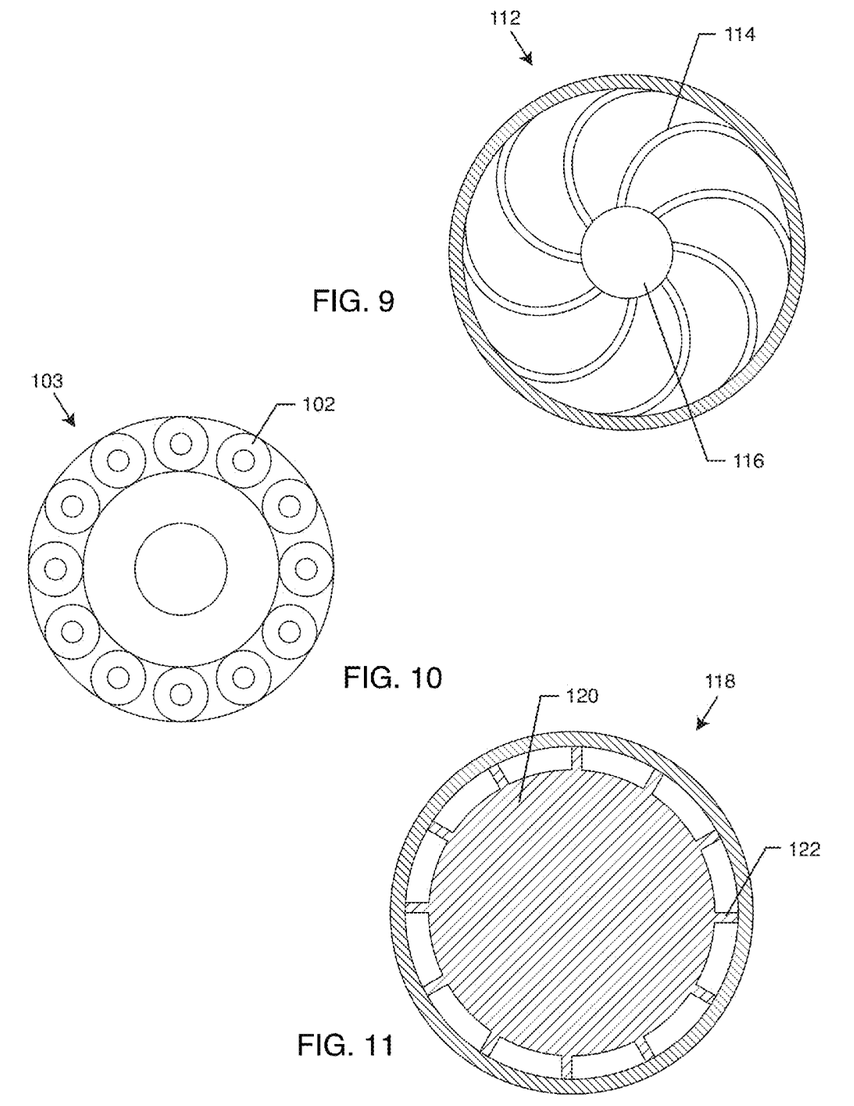
FIG. 9 is a cross-sectional view of the turbulizer disk taken along line 9-9 of FIG. 8.
FIG. 10 is a cross-sectional view of the radial multi-jet nozzle taken along lines 10-10 of FIG. 8.
FIG. 11 is a cross-sectional view of the cylindrical body taken along lines 11-11 of FIG. 8.
Figure 12:
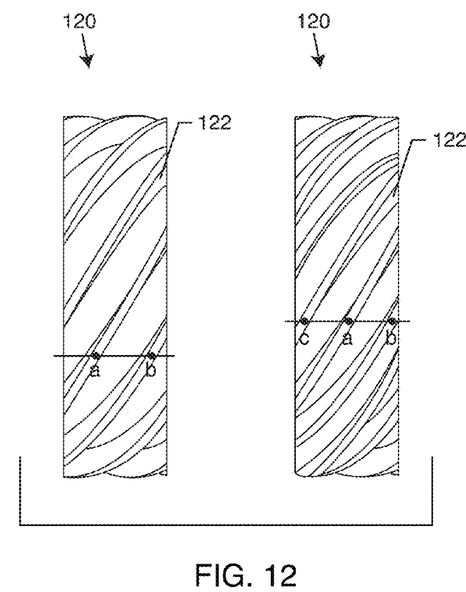
FIG. 12 is a side view of the cylindrical body.
Figure 13:
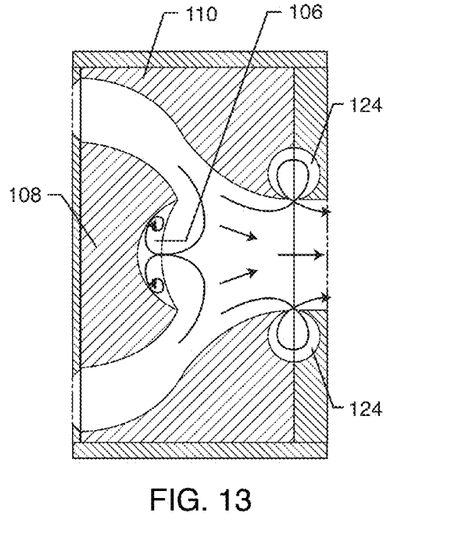
FIG. 13 is a close-up view of the front interior working chamber and toroidal vortex chamber illustrating fluid flow.
Figure 14:
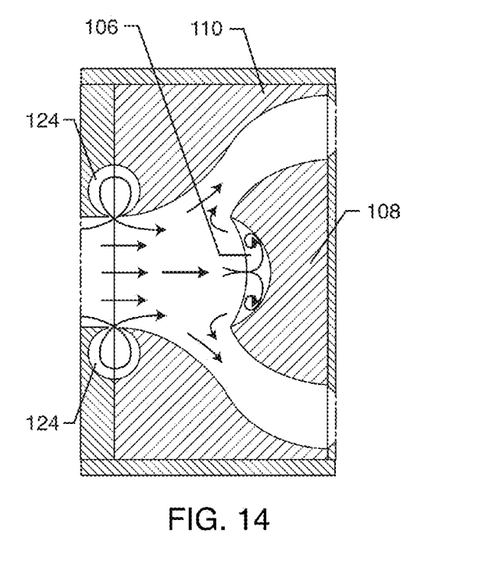
FIG. 14 is a close-up view of the back interior working chamber and toroidal vortex chamber illustrating fluid flow.
Figure 15:
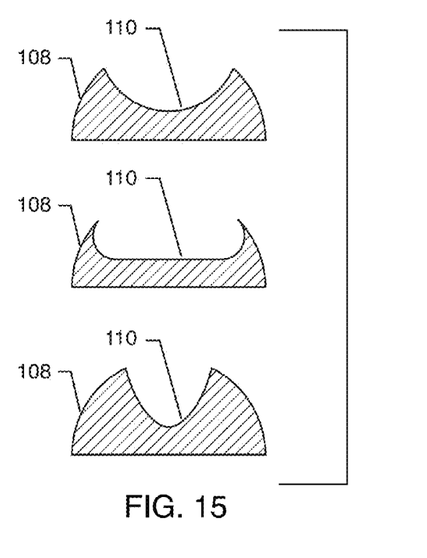
FIG. 15 is a cross-sectional view of various forms of the hemi-spherical body.

FIG. 9 is a diagram that shows disks 112a, 112b with curved guides 114 and central hole 116. An interior side of the radial multi-jet nozzles 100 is depicted in FIG. 10. The channels 102 let out into the interior working chambers 104 housing the hemi-spherical body 108 having top niche 110. FIG. 11 shows a cross-sectional view of the cylindrical body 120, which is provided with the superficial perimeter guides 122 that serve as the channels for fluid flow. FIG. 12 is a drawing of a preferred embodiment for the guides 122 of the cylindrical body 120. FIGS. 13 and 14 depict the junction between the interior working chambers 104 and the disks 112 and illustrate fluid flow therein. At the junction between the guides 106 and the disks 112 are toroidal vortex chambers 124 which are connected to the holes 116 and interior working chambers 104. FIG. 15 is a simplified schematic illustration showing various embodiments for the niche 110 in the hemispherical body 108: a hemi-sphere, a toroid, and a parabola.

Figure 16:
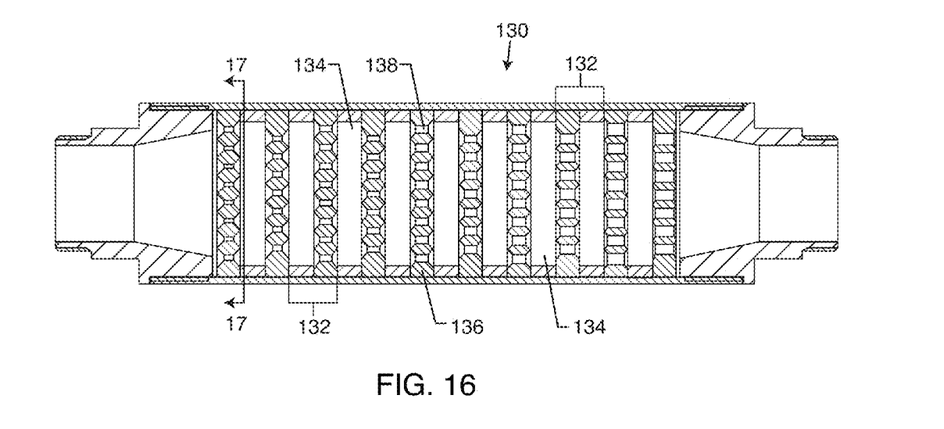
FIG. 16 is a cross-sectional view of another preferred embodiment of the multi-stage flow-through hydrodynamic cavitation device.

FIG. 16 is a drawing that illustrates another alternate embodiment for a flow-through multi-stage cavitation device 130 that provides as many as ten zones 132 for generation and collapse of cavitation bubbles and is comprised of ten identical working chambers 134 and ten multi-jet nozzles 136 that differ in respect to the cross-sectional passage areas created by their channels 138.

Figure 17:
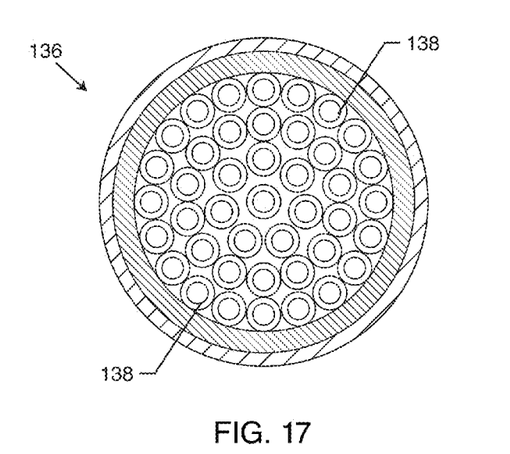
FIG. 17 is a cross-sectional view taken along line 17-17 of FIG. 16.

FIG. 17 illustrates the nozzles 136 and the channel 138 therein. The total cross-sectional channel area ($S_n$) of each multi-jet nozzle is less than that of the next multi-jet nozzle ($S_{n+1}$) following the flowpath, according to the equation: $1.0 \leq S_{n+1}/S_n \leq 1.1$, where n=1, 2, 3, 4, 5, 6, 7, 8 or 9. This helps save energy required for pumping a fluid flow through the multi-zone cavitation system. To scale back the cavitation device parts, for example, the multi-jet nozzle 136, it is necessary to place the channels 138 for fluid passage as close as possible. The number of the channels 138 of the multi-jet nozzle 136 is limited by the ratio of the total area of the largest cross-sectional openings of the channels ($S_d$) to the surface area of the multi-jet nozzle ($S_D$): $S_d/S_D \leq 0.8$, where $$S_d = \sum_{i=1}^{k} S_i(k$$

is the number of channels of the multi-jet nozzle; $S_i = \pi d_i^2/4$, where $d_i$ is the largest diameter of the channels I, and $S_D = \pi D^2/4$, where D is the multi-jet nozzle diameter.

The cavitation device 30 used in the inventive method can be fabricated from many materials, which should be easy to fabricate, able to withstand both elevated pressure and increased temperature, and exhibit high resistance to corrosion, thus allowing the device to be exploited continuously and repeatedly. In addition, the materials should be mechanically compatible to assure similar properties of material expansion upon heating.

In one preferred embodiment of the invention, the device 30 is made of a hardened stainless steel. The inner walls are preferably coated to increase the wear resistance and enhance resistance to corrosive chemicals, protect the valuable intracellular extractable by-products from denaturation and decomposition and/or fulfill desired chemical modifications. The coating is preferably aluminum, chromium, copper, copper-nickel, boron, boron-copper, boron-nickel, nickel, ceramics, plastics, polytetrafluoroethylene, tungsten carbide, acrylics, epoxies, polyurethanes, polyesters, nanotubes, detonation-synthesized surface-modified and non-modified nanodiamonds (Grichko et al., 2008), and other suitable materials. The inner surface may also be roughened to increase the degree of cell disintegration. The surface can be hardened and its properties can be further perfected via anodizing, bonding, chromating, electrocoating, thermal spraying, plasma coating, plasma electrolytic oxidation, electrolytic deposition or using another suitable technology.

To be fully effective the catalyzed cavitation should generate cavities that collapse at the surface of the catalyst or in the vicinity of it. In another embodiment, a transesterification catalyst or/and lipases and/or other enzymes are supported by magnetic particles or immobilized onto their surface (Mahmood et al., 2008; Marchetti and Errazu, 2008). The particles can self-attach to the inner walls of the device at any desired location to enhance the processing outcome. The cavitation chambers may be made of magnetic material and/or be provided with the walls coated with the magnetic material. The device can be subjected to an external permanent, alternative, or pulsed electric and/or magnetic field during the cavitation process.

Both the inner and outer system dimensions depend upon the intended use of the device. A small cavitation system is preferable when the amount of medium to be cavitated is limited, its cost is high or rate of algal oil production is intended to be low. Large systems with an inner diameter of 10 inches or larger generate larger cavities and provide a high treatment throughput. In a preferred embodiment, the cylindrical cavitation device 30 is approximately fourteen inches long with an outside diameter of about three inches. To enhance mixing and cavitation the channels 48 of the multi-jet nozzle 40 are uniquely shaped and contain both contractions and expansions. More particularly, the cross-sectional diameters of the channels 48 vary along the fluid path. The channels 48 can be fabricated in the shape of Venturi nozzles to separate vortices and generate pressure pulsations at the characteristic frequencies. The Venturi nozzle generates unsteady flow that can be calculated by those skilled in the art (Fedotkin and Gulyi, 2000; Mahesh et al., 2004; Li et al., 2008).

The disintegration of algal microorganisms using the flow-through hydrodynamic cavitation device 30 is followed by a separation process, i.e., sedimentation, centrifugation, filtration, vaporization, distillation, freezing, extraction, washing or any other similar downstream step in order to recover the algal oil and collect the valuable by-products. For example, the by-products, i.e., cell debris, can be pressed into pellets that have a high nutrient value and can be used for animal feed or to produce supplements, vitamins, beauty products or pharmaceuticals. In another embodiment of the present invention, the residual slurry is used for manufacturing plastics, resin, composite materials and other high-value products. In other embodiments, the silicon- or sulfur-enriched residual slurry of the present invention is employed in the synthesis and making of cross-linking agents and materials.

In another embodiment, the algal cell disruption is coincidental or is followed by other cavitation events to drive chemical reactions. The bubbles generated before or during these events are comprised of the vapors of all compounds that are volatile under the process conditions, including those extracted from the destroyed microorganisms. In one embodiment of the present invention, methanol is used as a cavitation solvent and when no significant concentration of water is present in the system, the catalyzed transesterification process can proceed. Energy released due to the implosion of bubbles during the flow-through hydrodynamic cavitation process activates molecules forcing them to react and form entirely new compounds. The result is the formation of the fatty acid metyl esters, the main constituents of biodiesel. In a similar way, other reactions whose products are stable can be performed. In this embodiment, algal cell disintegration and biodiesel production are carried out almost simultaneously, preferably during one pass of the medium of the preliminary dried algal microorganisms through the cavitation device.

The size of the cavities formed during cavitation processing depends on the physical and chemical properties of the cavitation fluid and the engineering design of the cavitation device, as well as other conditions, such as the flow velocity sustained by the hydrolytic pump. In practice, the pump pressure is increased until a proper cavitation field is achieved. In addition to determining the size, concentration and vapor composition of cavities, and, as a consequence, the amount of released energy, the inlet pressure determines the extraction yield and composition of the processed medium.

The higher the flow rate, the smaller the cavitation number. A lower cavitation number (especially those less than 1) implies a higher degree of cavitation. The preferred embodiment of the present invention optimizes the cavitation to uniformly alter algae-enriched media by applying the most suitable pump pressure, selected from a range of approximately 50-5,000 psi. However, if too much energy is applied or the residence time is too long, then the equipment cost increases. The desirable outcome is produced by generating hydrodynamic cavitation at a pump pressure designed to cause cavitation and disruption of algal microorganisms consistently throughout the medium.

The device 30 is used for carrying into effect the method, according to the present invention. In accordance with the present invention, an algae-containing medium is treated either continuously or periodically, by passing through the multi- or one-stage cavitation unit or multi-unit system. The apparatus may be placed fixed or moveable at any algae production site, near a water-filled container, a naturally existing body of water, or a cell-growth reactor or photobioreactor. The flow-through hydrodynamic devices are designed to treat large volumes of process fluids at ambient temperature and pressure. Additional lines and skid systems can be added or one device may be combined with another device to scale up production capacity. These systems can be easily mounted and transported, making them suitable for production in the field. In practice, it is necessary to take into account the device cost, its production capacity and the subsequent energy, maintenance and operation cost. It should be emphasized, that an operator of the cavitation device is not required to wear the safety products for hearing protection, such as earmuffs or earplugs, as it would be in the case of high-frequency cavitation.

The implosion of cavities is accompanied by the formation of deformed microbubbles. The pressure and temperature of vapors contained in them are very high. As fluid enriched with these microbubbles moves into a reduced-pressure zone, they will become nuclei, expand and become cavitation bubbles, enhancing the field intensity. The bubble multiplication, expansion, pulsation and implosion lower the cavitation threshold, because bubbles originate from the vapor nuclei, whose volume is larger than that of the fluid nuclei. When fluid is subjected to consecutive cavitations, it is heated up and gets enriched with those nuclei. This intensifies processing and allows selective chemical reactions to be carried out while targeting compounds extracted from the algal cells. This makes this embodiment unique and especially suitable for the oil recovery from algae or other cells of high economical value. With sonic and ultrasonic radiation, the outcome is mixed unless cavitation is uniform throughout the volume. However, creating even acoustic cavitation in large commercial tanks is a particular challenge as mentioned above.

The present device achieves extraction of oil from algae through use of a flow-through hydrodynamic cavitation. In accordance with the preferred embodiment of the present invention cavitation is generated at a pump pressure of approximately 50-5,000 psi. Therefore, a practical approach to the best process yield is to establish a pressure that provides enough bubble implosion energy for disruption and mixing. The optimal pressure produces cavities in sufficient concentration to achieve a high degree of extraction. However, one familiar with the art will understand that different media and cells require different energies in order for their disruption to occur. Therefore, the range of 50-5,000 psi is not intended to limit the use of the present invention.

The application of the flow-through hydrodynamic cavitation is not limited to the recovery of oil from algae. The invention may have further applications in the purification of water, which is infested with Chlorophyceae or other algae species, including natural water reservoirs, ponds, lakes, pools, fountains, commercial water-storage containers and other water bodies. It has been reported that jet cavitation does not destroy only inhibits growth of *Microcystis aeruginosa* with the outcome strongly dependent on the inlet pressure, cavitation number, light and algae concentration (Xu et al., 2006). Similarly, acoustic cavitation results in a loss of buoyancy. The ultrasound waves act upon the gas vesicles, collapsing vacuoles, damaging chlorophyll and precipitating Chlorophyceae and *Spirulina platensis* (Hao et al., 2004; Dehghani and Changani, 2006). Apart from these technologies, the flow-through hydrodynamic cavitation available through the present invention allows one to recover algal oil and modify it, if needed.

The present invention creates beneficial conditions that cannot be duplicated. The process efficiency is high and can be enhanced by consecutive applications of high pressure, elevated heat, turbulence and vigorous mixing applied in a flow-through manner within a short period. The preferred embodiments of the present invention apply optimized levels of both pressure and temperature via a controlled flow-through hydrodynamic cavitation. The process is independent of external conditions and provides a highly effective means of cell disruption, oil extraction and changing medium composition and properties evenly throughout the flow. Important economic benefits are experienced through implementation of the present invention. The optimized usage of a flow-through hydrodynamic cavitation device serves to lower equipment, handling and energy costs, as it improves the efficiency of algal oil recovery.

Figure 18:
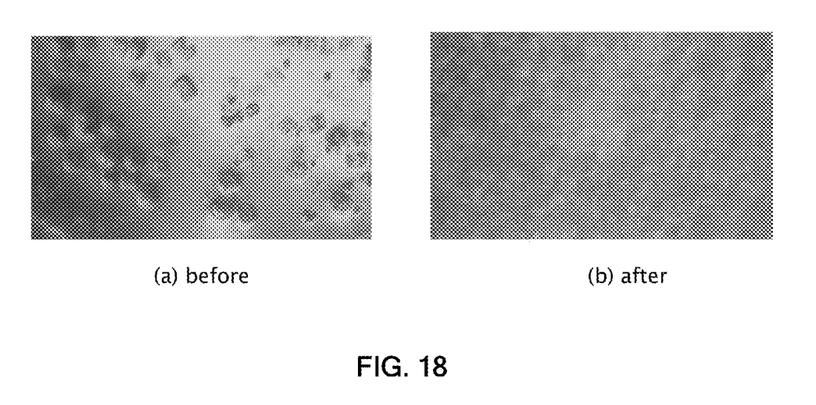
FIG. 18 is a set of pictures of a broth containing algal microorganisms before and after processing in a flow-through hydrodynamic cavitation device according to the present invention.

The following example is given for illustrating the present invention and should not be construed as a limitation on either the scope or spirit of the invention. Four gallons of a high-density aqueous algal culture were subjected to a single-pass cavitation in a device 30 at a pump pressure of 800-psi. Using Sedgwick-Rafter counting chambers and an optical microscope, it was determined that 99% of the algal cell had been disintegrated by the cavitation treatment. FIG. 18 presents pictures of a broth containing algal microorganisms before and after processing in a flow-through hydrodynamic cavitation device 30 according to the present invention. The high degree of disintegration of the algal cells in the after photo is readily apparent to one skilled in the art.

A method of generating micro bubbles in a liquid algae microorganism medium and disintegrating of said microorganisms, comprises feeding the medium into the flow-through hydrodynamic cavitation device, controlling the cavitation by setting an inlet pump pressure, and continuing the application of such cavitation for a period of time sufficient for the proper degree of disruption of the algae, followed by recovering the intracellular oil. The definition of "algal microorganism medium" includes, but is not limited to a heterogeneous complex medium, containing any types of algae species, wild-type species, mutated or genetically altered species or mixtures thereof that are vital, vegetative, dead, dried, intact and/or broken cells or the algae microorganisms in any other state or condition or mixture thereof. Said medium may be solid and can be made liquid immediately prior to the cavitation or be a two- or multi-phase system comprised of unmixable liquids, solution of salts, gases and/or other solutes, dispersion, emulsion, suspension, melted solid, gas in a supercritical condition or mixture thereof.

The detailed embodiments of the present invention are disclosed herein. However, it should be understood that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and how to use the present invention. Although several embodiments have been described in detail for purposes of illustration, various modifications may be made without departing from the scope and spirit of the invention.

What is claimed is:

1. A method for processing an algae medium containing algae microorganisms to produce algal oil and by-products, comprising the steps of:
    providing a flowpath through a multi-stage, flow-through, hydrodynamic cavitation device, wherein each stage comprises a separate localized zone having a contraction of the flowpath;
    pumping the algae medium through a plurality of channels in a multi-jet nozzle in a first localized zone, the plurality of channels presenting the contraction of the flowpath in the first localized zone;
    passing the algae medium through a plurality of spiral guides disposed in a working chamber with a decreasing diameter in a second localized zone, wherein the plurality of spiral guides have a decreasing pitch following the decreasing diameter presenting the contraction of the flowpath in the second localized zone;
    conveying the algae medium through a plurality of flow guides and a vortex generator in a third localized zone, wherein the flow guides and vortex generator create an annular gap presenting the contraction of the flowpath in the third localized zone;
    disintegrating cell walls of and intracellular organelles in the algae microorganisms through the pumping, passing and conveying steps to produce algal oil and by-products; and
    introducing the algae medium to an atomizing cone in the flowpath, the atomizing cone having an increasing cross-sectional area along the flowpath, wherein the algae medium loses all cavitational features.

2. The method of claim 1, wherein the pumping step comprises the steps of:
    generating an area of reduced fluid pressure in the algae medium resulting from being pumped through the contraction of the flowpath in the first localized zone, such contraction resulting in increased flow velocity which causes a reduction in fluid pressure;
    creating cavitational vapor bubbles of volatile compounds in the algae medium resulting from the area of reduced fluid pressure, wherein the volatile compounds form vapors at the reduced fluid pressure;
    collapsing the cavitational vapor bubbles as the algae medium leaves the first localized zone exposing components of the algae medium in the cavitational vapor bubbles and the surrounding fluid to sudden, localized increases in temperature and pressure; and
    forming microbubbles in the algae medium following collapse of the cavitational vapor bubbles, which microbubbles are nuclei for the creation of cavitational vapor bubbles in a subsequent localized zone.

3. The method of claim 1, wherein the passing step comprises the steps of:
    generating an area of reduced fluid pressure in the algae medium resulting from being passed through the contraction of the flowpath in the second localized zone, such contraction resulting in increased flow velocity which causes a reduction in fluid pressure;
    creating cavitational vapor bubbles of volatile compounds in the algae medium resulting from the area of reduced fluid pressure, wherein the volatile compounds form vapors at the reduced fluid pressure;
    collapsing the cavitational vapor bubbles as the algae medium leaves the second localized zone exposing components of the algae medium in the cavitational vapor bubbles and the surrounding fluid to sudden, localized increases in temperature and pressure; and
    forming microbubbles in the algae medium following collapse of the cavitational vapor bubbles, which microbubbles are nuclei for the creation of cavitational vapor bubbles in a subsequent localized zone.

4. The method of claim 1, wherein the conveying step comprises the steps of:
    generating an area of reduced fluid pressure in the algae medium resulting from being conveyed through the contraction of the flowpath in the third localized zone, such contraction resulting in increased flow velocity which causes a reduction in fluid pressure;
    creating cavitational vapor bubbles of volatile compounds in the algae medium resulting from the area of reduced fluid pressure, wherein the volatile compounds form vapors at the reduced fluid pressure;
    collapsing the cavitational vapor bubbles as the algae medium leaves the third localized zone exposing components of the algae medium in the cavitational vapor bubbles and the surrounding fluid to sudden, localized increases in temperature and pressure; and forming microbubbles in the algae medium following collapse of the cavitational vapor bubbles.

5. The method of claim 1, further comprising the step of separating the algal oil from the algae medium.

6. The method of claim 1, wherein the algae medium comprises algal microorganisms suspended in methanol, ethanol, butanol or a mixture thereof.

7. The method of claim 6, further comprising the step of adding vegetable oil and/or animal fat or tallow to the algae medium prior to the pumping step.

8. The method of claim 1, further comprising the step of adding hydrogen peroxide, salts, acids, bases, buffers, detergents and/or enzymes to the algae medium prior to the pumping step.

9. The method of claim 8, further comprising the steps of:
adding a transesterification catalyst to the algae medium prior to the pumping step; and
reacting triglycerides, diglycerides, monoglycerides, and fatty acids in the algal oil with an alcohol in the flow-through, hydrodynamic cavitation device to produce fatty acid esters.

10. The method of claim 9, wherein inner walls of the flowpath are made from or coated with aluminum, chromium, copper, copper-nickel, boron, boron-copper, boron-nickel, nickel, ceramics, plastics, polytetrafluoroethylene, tungsten carbide, acrylics, epoxies, polyurethanes, polyesters, nanotubes, detonation-synthesized surface-modified and non-modified nanodiamonds, a metal, a metal alloy, a solid transesterification/esterification catalyst, or a magnetic material.

11. A method for processing an algae medium containing algae microorganisms to produce algal oil and by-products, comprising the steps of:
introducing the algae medium to an inlet on a multi-stage, flow-through, hydrodynamic cavitation device;
passing the algae medium through a flowpath in the hydrodynamic cavitation device, the flowpath having at least ten cavitation zones;
exposing the algae medium to cavitation inducing features in each of the at least ten cavitation zones to create cavitational vapor bubbles therein;
collapsing the cavitational vapor bubbles between every two adjacent of the at least ten cavitation zones;
disintegrating cell walls of and intracellular organelles in the algae microorganisms through the passing, exposing and collapsing steps to produce algal oil and by-products; and
removing the algae medium from an outlet on the hydrodynamic cavitation device.

12. The method of claim 11, wherein the exposing step comprises the steps of:
generating an area of reduced fluid pressure in the algae medium resulting from being pumped through a contraction of the flowpath in each of the at least ten cavitation zones, such contraction resulting in increased flow velocity which causes a reduction in fluid pressure; and
creating cavitational vapor bubbles of volatile compounds in the algae medium resulting from the area of reduced fluid pressure, wherein the volatile compounds form vapors at the reduced fluid pressure.

13. The method of claim 11, wherein the collapsing step further comprises the step of forming microbubbles in the algae medium following collapse of the cavitational vapor bubbles, which microbubbles are nuclei for the creation of cavitational vapor bubbles in a subsequent cavitation zone.

14. The method of claim 11, further comprising the step of separating the algal oil from the algae medium.

15. The method of claim 11, wherein the algae medium comprises algal microorganisms suspended in methanol, ethanol, butanol or a mixture thereof.

16. The method of claim 15, further comprising the step of adding vegetable oil and/or animal fat or tallow to the algae medium prior to performing the passing step.

17. The method of claim 11, further comprising the step of adding hydrogen peroxide, salts, acids, bases, buffers, detergents and/or enzymes to the algae medium prior to performing the passing step.

18. The method of claim 17, further comprising the steps of:
adding a transesterification catalyst to the algae medium prior to the passing step; and
reacting triglycerides, diglycerides, monoglycerides, and fatty acids in the algal oil with an alcohol in the flow-through, hydrodynamic cavitation device to produce fatty acid esters.

19. The method of claim 18, wherein inner walls of the flowpath are made from or coated with aluminum, chromium, copper, copper-nickel, boron, boron-copper, boron-nickel, nickel, ceramics, plastics, polytetrafluoroethylene, tungsten carbide, acrylics, epoxies, polyurethanes, polyesters, nanotubes, detonation-synthesized surface-modified and non-modified nanodiamonds, a metal, a metal alloy, a solid transesterification/esterification catalyst, or a magnetic material.

* * * * *